Figure 1:
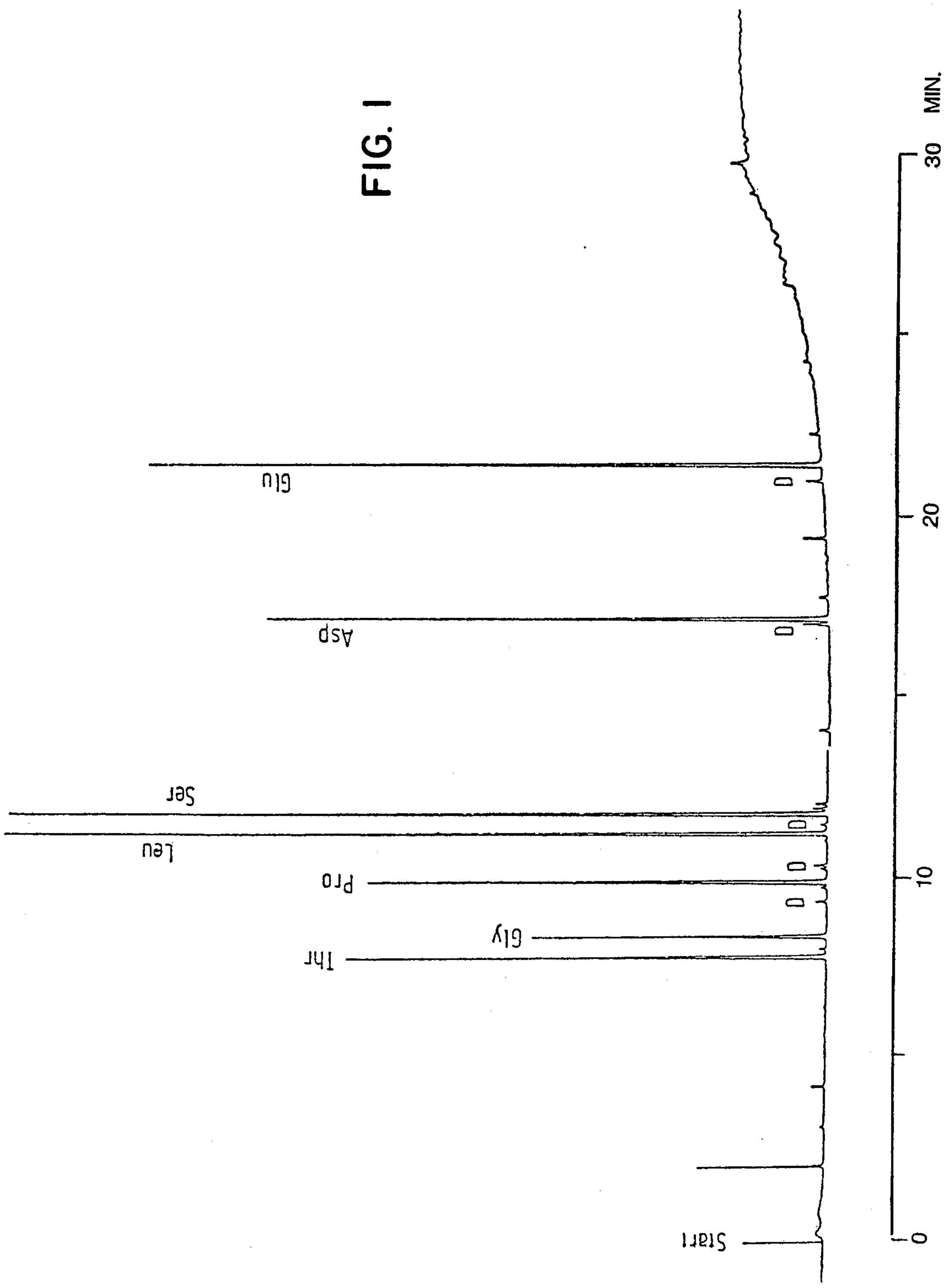

United States Patent [19]

Jung et al.

[11] 4,370,312

[45] Jan. 25, 1983

[54] DECAPEPTIDE

[75] Inventors: Günther Jung, Tübingen; Hans Brückner, Ostfildern/Nellingen, both of Fed. Rep. of Germany; Peter Swetly, Vienna, Austria; Gerhard Bozler, Biberach an der Riss, Fed. Rep. of Germany

[73] Assignee: Dr. Karl Thomae Gesellshaft mit beschrankter Haftung, Biberach an der Riss, Fed. Rep. of Germany

[21] Appl. No.: 315,213

[22] Filed: Oct. 26, 1981

[30] Foreign Application Priority Data

Oct. 30, 1980 [DE] Fed. Rep. of Germany ....... 3040824

[51] Int. Cl.[3] ..................... G01N 33/00; A61K 39/00; C07C 103/52

[52] U.S. Cl. ....................................... 424/1.5; 424/85; 260/112.5 R

[58] Field of Search ................................. 424/1.5, 85; 260/112.5 R

[56] References Cited

PUBLICATIONS

K. C. Zoon, et al., "Science" 207, 1980, 527, 528.
E. Knight, Jr., et al., "Science" 207, 1980, 525, 526.

*Primary Examiner*—Delbert R. Phillips
*Attorney, Agent, or Firm*—Hammond & Littell, Weissenberger & Muserlian

[57] ABSTRACT

The decapeptide of the formula

H-Ser-Asp-Leu-Pro-Gln-Thr-His-Ser-Leu-Gly-OH and the use thereof as hapten, tracer or antibody.

6 Claims, 5 Drawing Figures

Boc-Ser(Bzl)-Asp(Bu$^t$)-Leu-Pro-Gln-Thr(Bzl)-His-Ser(Bzl)-Leu-Gly-NHNH$_2$ $^{13}$C-NMR (20.115 MHz, in Methanol), 10 - 85 ppm $^{13}$C-NMR (10-70 ppm) of LIF1-10 in $^{2}H_{2}O$ FIG. 3B
Ser-Asp-Leu-Pro-Gln-Thr-His-Ser-Leu-Gly
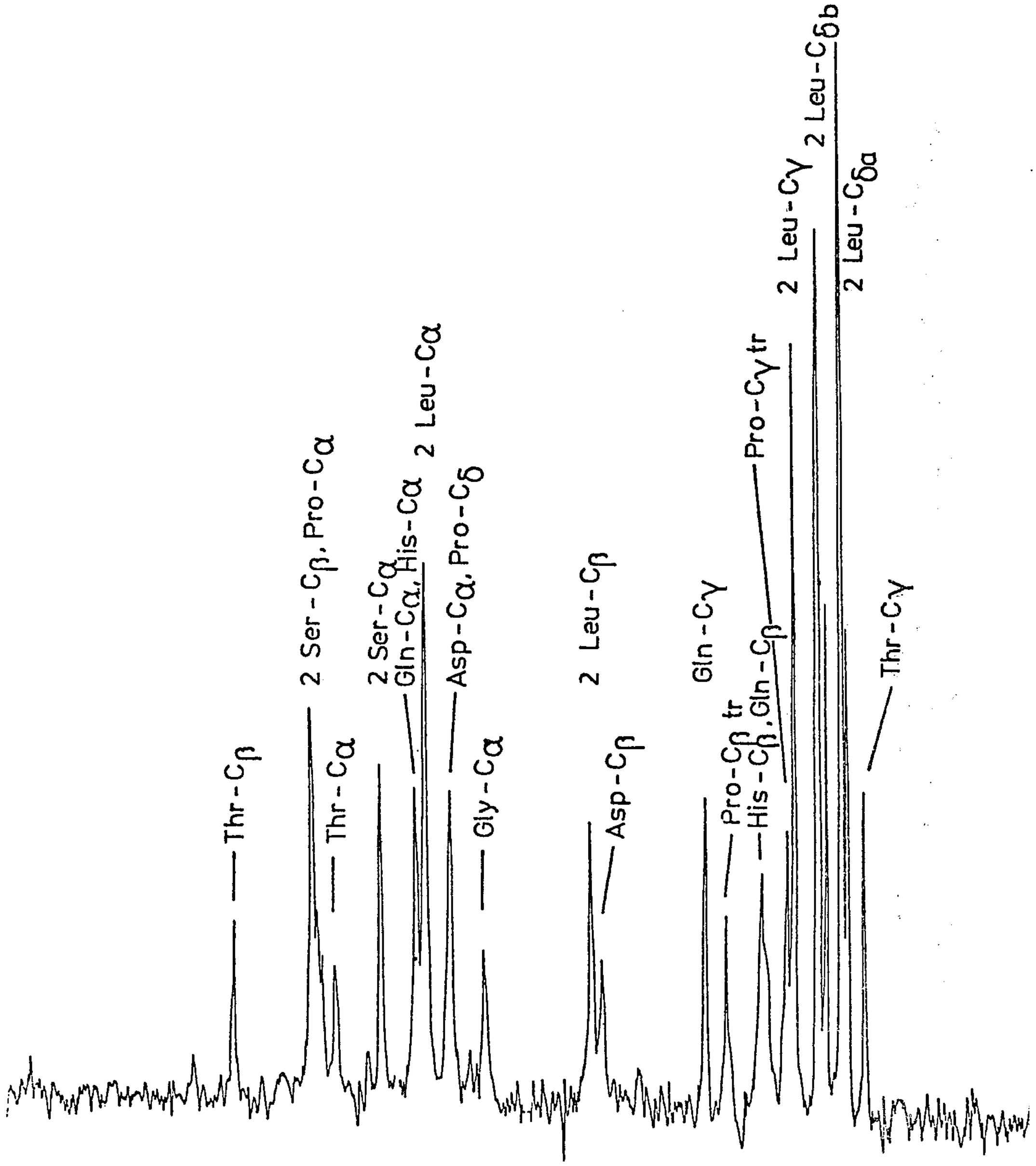

DECAPEPTIDE

This invention relates to a novel decapeptide, to a process for its preparation by the solid-phase-synthesis, and to a method of using it as a hapten for coupling with an immunogen, for example.

The following conventional abbreviations used in peptide chemistry shall be used hereinafter:

H-Ser-OH=L-Serine
H-Asp-OH=L-Aspartic acid
H-Leu-OH=L-Leucine
H-Pro-OH=L-Proline
H-Glu-OH=L-Glutamic acid
H-Thr-OH=L-Threonine
H-His-OH=L-Histidine
G-Gly-OH=Glycine
Bzl=Benzyl radical
Dnp=2,4, -Dinitrophenyl radical
Boc=tert. Butyloxycarbonyl radical
Fmoc=9-Fluorenylmethyloxycarbonyl radical
But=tert. Butyl radical
DMF=Dimethylformamide
DCC=N,N'-Dicyclohexylcarbodiimide
HOBt=1-Hydroxybenzotriazole Thus, the present invention relates to the novel decapeptide H-Ser-Asp-Leu-Pro-Glu-Thr-His-Ser-Leu-Gly-OH.

BACKGROUND OF THE INVENTION

Highly purified interferon, which is a very interesting substance and is being investigated throughout the world, is today available for medical research only in very small amounts. Therefore, it has heretofore not been possible to subject interferon-proteins to structural or biochemical investigations. Since the N-terminal sequence of human lymphoblast-interferon has now been elucidated [Science 207, 527 (1980)], the decapeptide of the instant invention has for the first time been synthesized and its properties investigated.

DESCRIPTION OF THE INVENTION

The decapeptide of the present invention is prepared by the solid-phase-synthesis [see Merrifield, J.A.C.S. 85, 2149–2154 (1963)]. In this method the C-terminal aminoacid of a peptide is attached by way of its carboxyl group to a polymer which serves as an insoluble carrier. If a chloromethyl-resin is used as the polymer, the attachment is effected either preferably by means of an alkali metal or alkaline earth metal salt of the corresponding N-protected aminoacid, or if a hydroxymethyl-resin is used as the polymer by activation of the carboxyl function of the corresponding N-protected aminoacid, for example with dicyclohexylcarbodiimide. This step is followed by the stepwise build-up of the peptide by stepwise attachment of the individual aminoacids to the N-end of the peptide fragment, and subsequent removal of the amino-protective group. The attachment of the next following N-protected aminoacid to the now free and reactive terminal amino group of the peptide fragment is effected by activation of its carboxyl function or by means of a reactive ester. After completion of the build-up of the aminoacid sequence the peptide is removed from the insoluble carrier resin. The presence of the aminoacids aspartic acid, serine, threonine and histidine requires the additional protection of the side-functions, for instance, by their conversion into the corresponding O-benzyl-threonine, O-benzyl-serine, N-im-2,4-dinitrophenylhistidine and aspartic acid β-tert. butyl ester derivatives.

A swellable polymer, such as a chloromethylated polystyrene which is preferably cross-linked with 1% divinylbenzene (PS-1% DVB), is preferably used in the solid-phase-synthesis of the present invention.

In a particularly advantageous embodiment of the process according to the present invention, glycine in its protected form, such as Boc-Gly-OH is esterified by means of its cesium salt as the first aminoacid onto chloromethylated polystyrene in a solvent, preferably in an aprotic solvent such as dimethylformamide. The cesium salt is advantageously obtained by reacting the above-mentioned protected aminoacid with cesium carbonate or cesium hydroxide. Thereafter, the amino-protective group which is used is split off; for instance, a tert. butoxycarbonyl group is removed with an acid such as 50% trifluoroacetic acid in dichloromethane, preferably after first washing with dichloromethane; or a Fmoc group is removed with diethylamine in dimethylformamide.

In each subsequent synthesis cycle the resulting product is coupled with an excess of the corresponding Boc- or Fmoc-aminoacid or its activated ester, for example with 3- to 6-fold the required amount, optionally in the presence of a coupling reagent such as N,N'-dicyclohexylcarbodiimide, and this procedure is repeated several times, such as 2 to 5 times, without prior testing for possibly still present free amino groups, with a further comparable excess of the corresponding Boc- or Fmoc-aminoacid and coupling reagent or its activated ester (post-coupling). After first washing, the Boc or Fmoc protective group is split off as described above.

This synthesis cycle is repeated with the particular N-protected aminoacids or their reactive esters until the desired protected decapeptide resin is obtained.

The aminoacid derivative Boc-Gln is preferably coupled by means of a reactive ester thereof, such as its p-nitro-phenyl ester. Furthermore, 1-hydroxy-benzotriazole may be added as a catalyst in the coupling or post-coupling procedures.

After each synthesis cycle the product is acetylated with acetic acid anhydride/N-methyl-morpholine to block, prior to the next coupling, any amino group of the peptide fragment which may have been left unreacted in the previous coupling procedure. Moreover, after the ninth coupling the Fmoc protective group is split off with a base such as diethylamine.

The partially protected decapeptide hydrazide is obtained after completion of the synthesis by addition of hydrazine to a suspension of the fully protected peptide resin in dimethylformamide. For further purification the hydrazide is reprecipitated, for instance from DMF/ether, whereby the yellow Dnp-products are substantially removed; chromatographed with methanol on a gel column, such as Sephadex LH 20; subjected to a reversed-phase chromatography on silicagel, such as silicagel RP-8, with methanol/water (90/10); and reprecipitated from methanol/ether.

After the synthesis is complete, the decapeptide free from protective groups is isolated by adding hydrogen bromide/glacial acetic acid to the suspension of the peptide resin in trifluoroacetic acid, with addition of resorcinol and thioanisole. At the same time, Boc, Bzl and O-$Bu^t$ groups are eliminated. After treatment of the resulting N-im-Dnp-His-decapeptide with mercaptoethanol and subsequent gel chromatography, for instance with Sephadex LH20, and reversed phase chromatography, for example on RP-8 silicagel, the free decapeptide is obtained.

Thus, the solid-phase-synthesis for the preparation of the partially protected decapeptide and the decapeptide free from protective groups is effected in accordance with the present invention pursuant to the following reaction scheme:

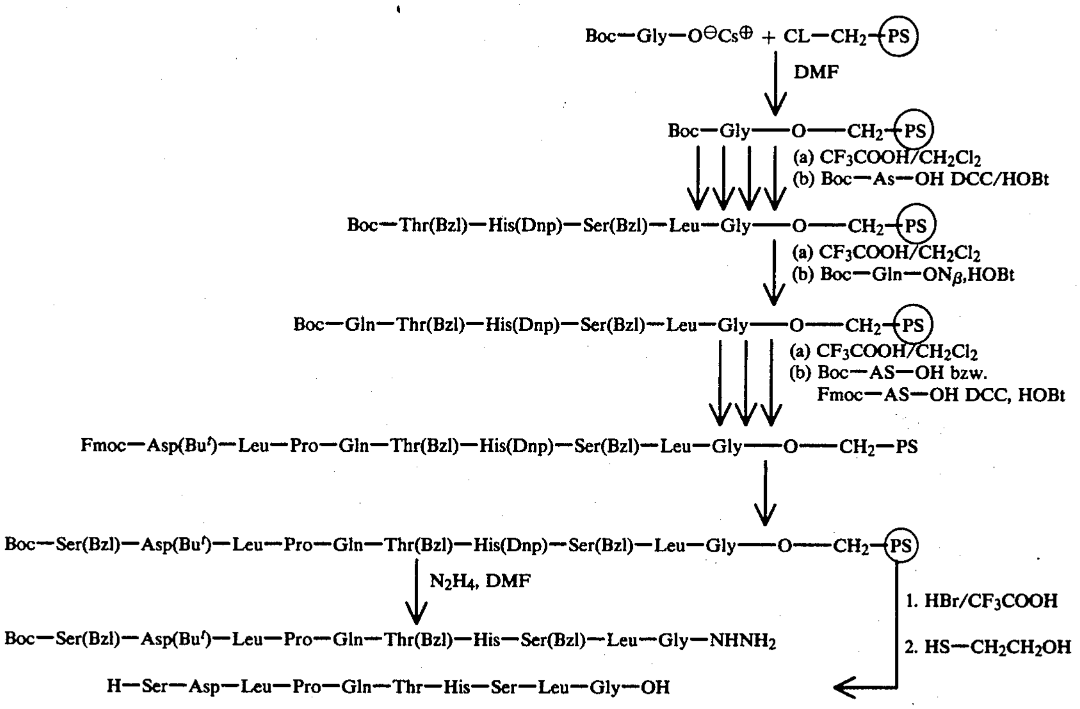

Figure 2A:
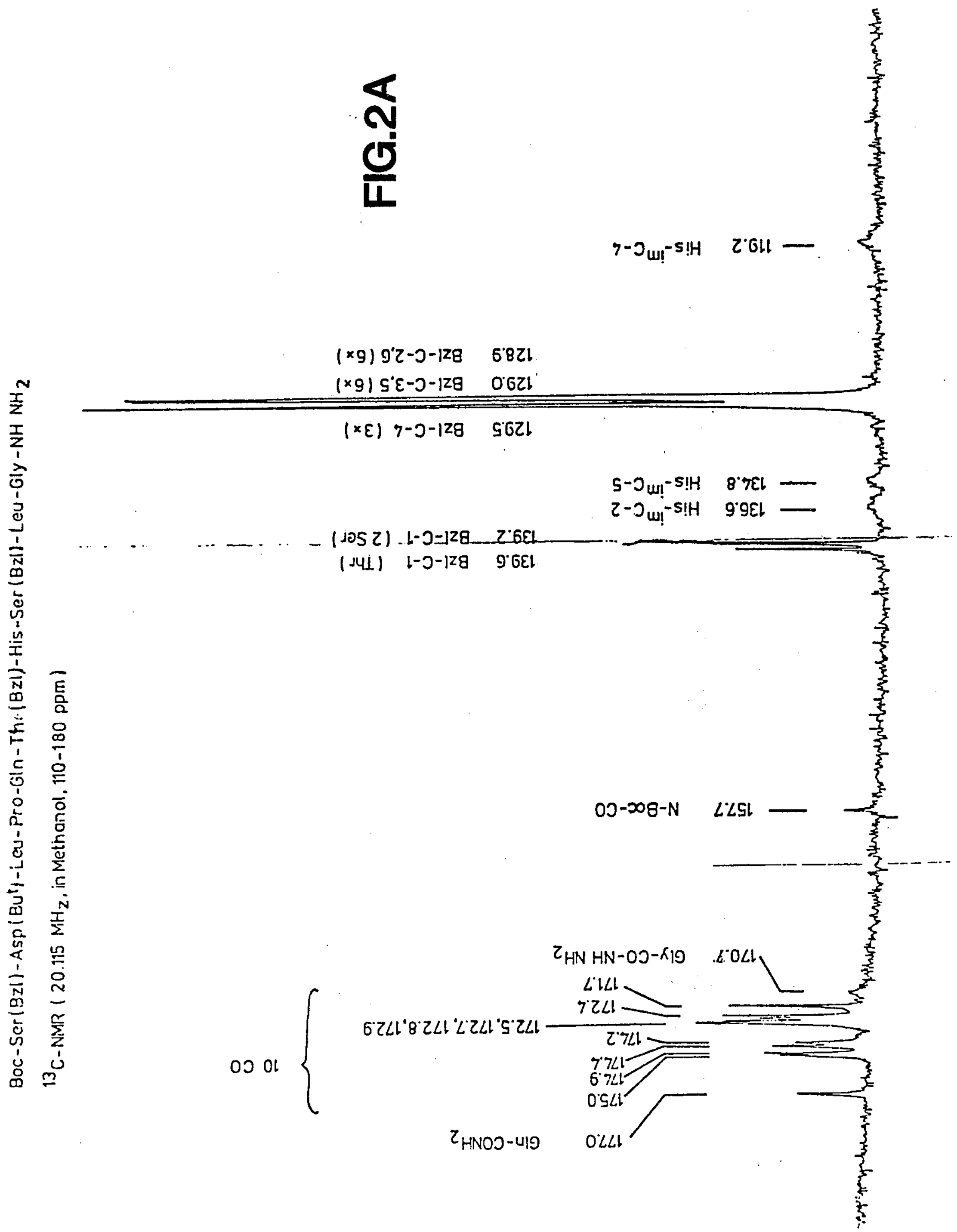
Figure 2B:
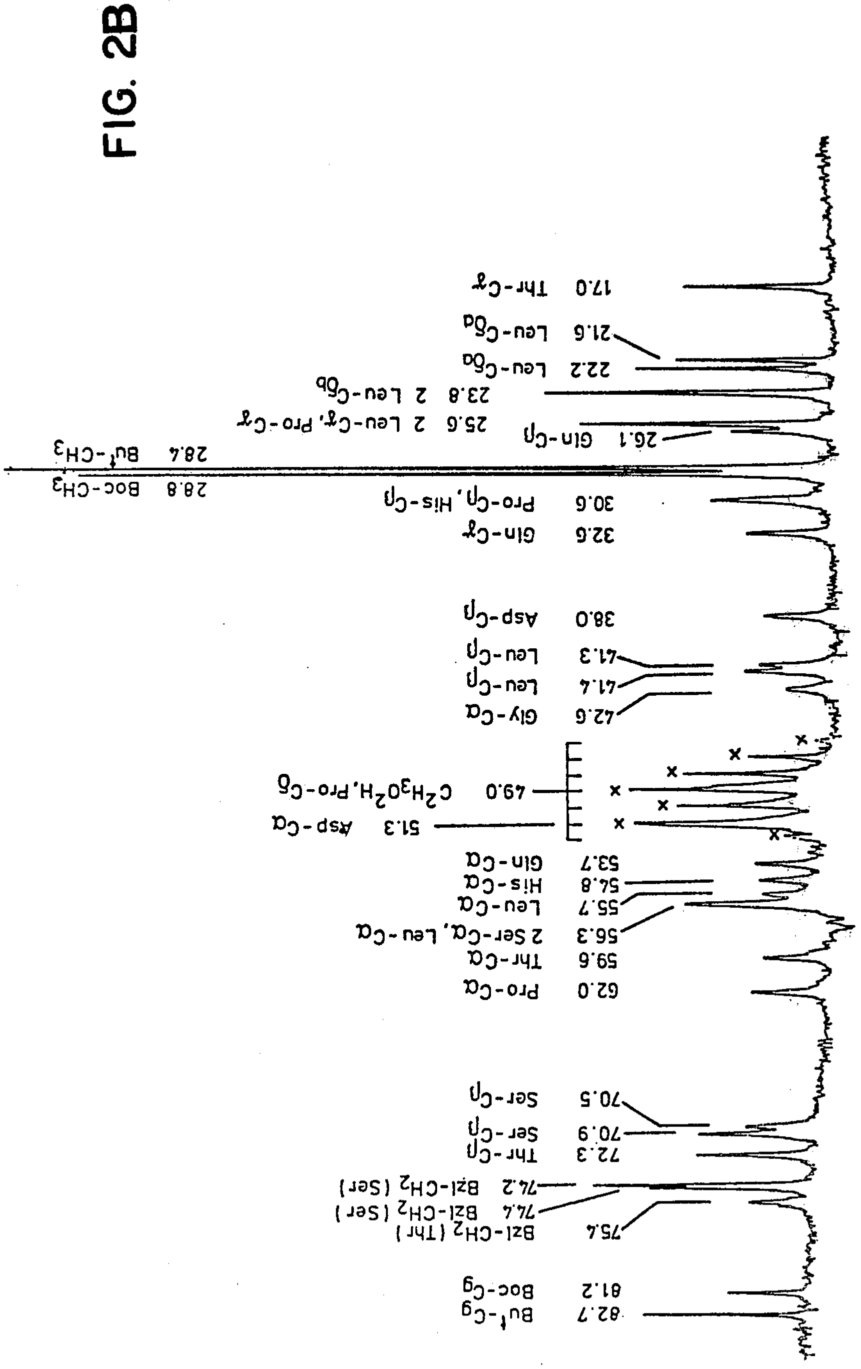
Figure 3A:
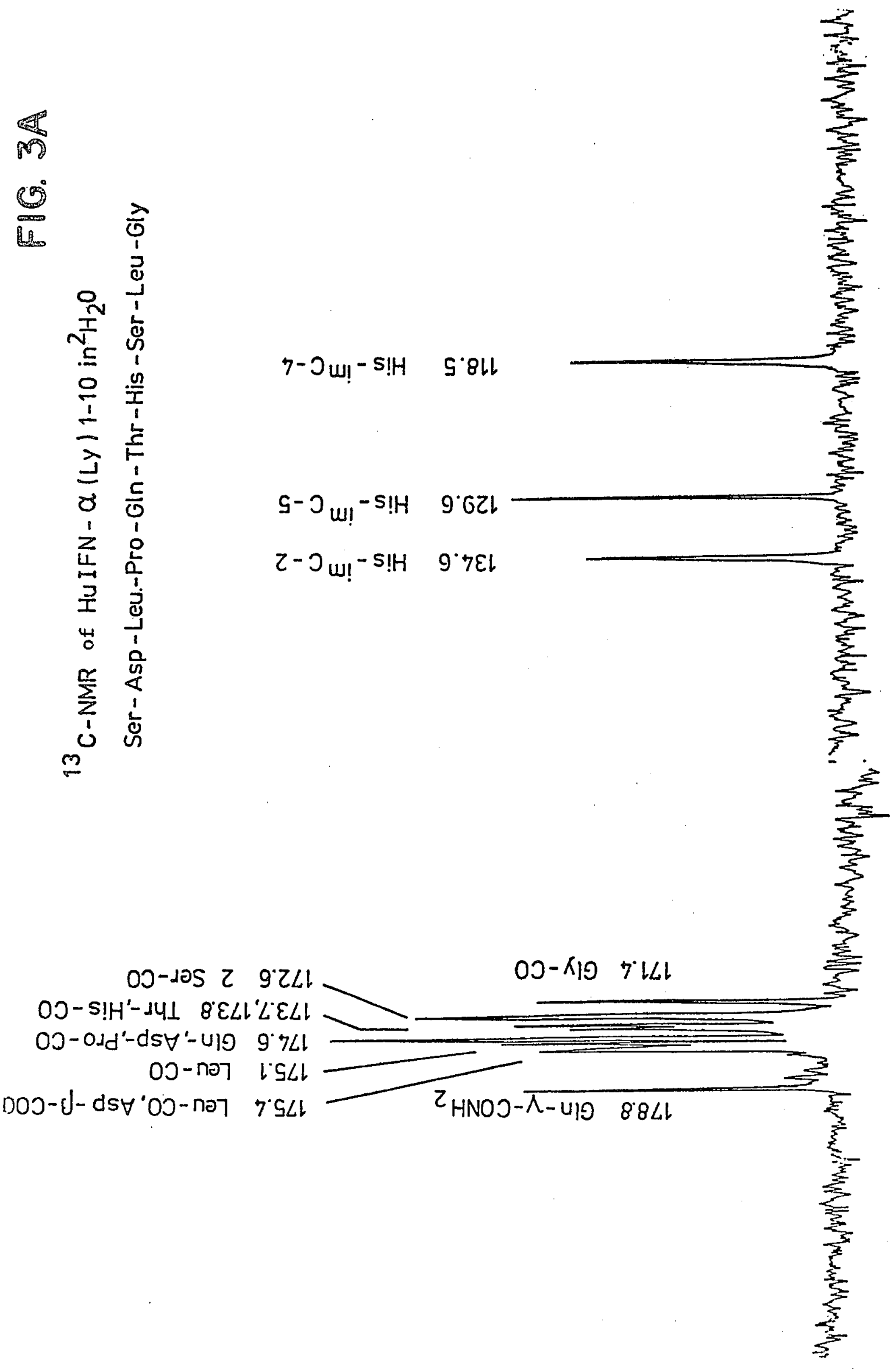

In the accompanying drawings:

FIG. 1 is the gas-chromatogram of the n-propyl esters of the N-pentafluoropropionyl-aminoacids of a hydrolyzate of the free decapeptide on chiral phase;

FIGS. 2*a* and 2*b* show the $^{13}C$-NMR spectra of the partially protected decapeptide hydrazide Boc-Ser(Bzl)-Asp(Bu$^t$)-Leu-Pro-Gln-Thr(Bzl)-His-Ser(Bzl)-Leu-Gly-$NHNH_2$; and FIGS. 3*a* and 3*b* show the $^{13}C$-NMR spectra of the decapeptide Ser-Asp-Leu-Pro-Gln-Thr-His-Ser-Leu-Gly.

The following examples illustrate the present invention and will enable others skilled in the art to understand it more completely. It should be understood, however, that the invention is not limited solely to the particular examples given below. Obviously, the decapeptide may also by synthesized in a similar manner using other condensation processes commonly used in peptide chemistry and other conventional protective groups.

EXAMPLE OF SOLID-PHASE-SYNTHESIS

I. Preparation of the decapeptide on the carrier

Stage 1

Esterification of N-tert. butoxycarbonyl-glycine with chloromethylated polystyrene:

15 gm of dry PS-1% DVB and 12.3 gm (40 mmols) of the cesium salt of N-tert.butoxycarbonyl-glycine were stirred in DMF at 50° for 28 hours. The product was then washed three times with DMF, DMF/water (9:1) and ethanol and dried in vacuo over phosphorus pentoxide. Measurement showed a charge of 0.4 mmol of Gly/gm.

Stage 2

After splitting off the Boc group with dichloromethane/trifluoroacetic acid (1:1) (reaction times of 1×2 minutes, 1×5 minutes) and neutralization with triethylamine in chloroform (1:5) (1×2 minutes, 1×5 minutes), coupling was effected with 7.5 gm (30 mmols) of Boc-Leu-OH×$H_2O$ (pre-dried), and post-coupling was effected with 7.5 gm (30 mmols) of Boc-Leu-OH×$H_2O$ analogous to Stage 3.

Stage 3

After splitting off the protective groups and neutralizing analogous to Stage 2, 5.9 gm (20 mmols) of Boc-Ser(Bzl)-OH were dissolved in 60 ml of dichloromethane and added to the dipeptide resin. Then, 20 ml (20 mmols) of a molar solution of DCC in dichloromethane were added. After 45 minutes, 5.9 gm (20 mmols) of BOC-Ser(Bzl)-OH in 60 ml of dichloromethane and 20 ml of DCC solution (1 molar in dichloromethane) were added for the first post-coupling. After 40 minutes, the product was washed twice with methanol/dichloromethane (1:4), twice with dichloromethane, once with 10% triethylamine in dichloromethane and 3 times with dichloromethane. For the second post-coupling, 5.9 gm (20 mmols) of BOC-Ser(Bzl)-OH in 60 ml of dichloromethane, 20 mmols of HOBt and 20 ml of DCC solution (1 molar in dichloromethane) were added, and the mixture was allowed to react for 60 minutes. The product was then washed three times with DMF, then reacted for 15 minutes with 6 ml of acetic acid anhydride in 40 ml of DMF and 3.3 ml of N-methylmorpholine in 40 ml of DMF, and then washed three times with DMF, three times with methanol/dichloromethane (1:4), three times with ethanol and three times with dichloromethane.

Stage 4

Coupling with 9.6 gm (20 mmols) of BOC-His(Dnp)-OH, post-coupling with 9.6 gm (20 mmols) of BOC- His(Dnp)-OH analogous to Stage 3. The Boc-His-(Dnp)-OH had to be dissolved in a little DMF before the dichloromethane was added.

Stage 5

Coupling with 6.18 gm (20 mmols) of BOC-Thr(Bzl)-OH, post-coupling with 6.18 gm (20 mmols) of BOC-Thr(Bzl)-OH analogous to Stage 3.

Stage 6

After splitting off the Boc protective group and neutralizing analogous to Stage 2, 22.0 gm (60 mmols) of BOC-Gln-Dnp were dissolved in 60 ml of DMF and added to the peptide resin. After half an hour, 8.1 gm (60 mmols) of HOBt were added, and the mixture was reacted for another 11 hours. Then, it was washed three times with DMF, three times with methanol and twice with DMF. It was then treated for 15 minutes with 6 ml of acetic acid anhydride and 3.3 ml of N-methylmorpholine in 60 ml of DMF. Subsequently, it was washed twice with DMF, three times with methanol and three times with dichloromethane.

Stage 7

Coupling with 4.3 gm (20 mmols) of Boc-Pro-OH, first post-coupling with 4.3 gm (20 mmols) of Boc-Pro-OH, second post-coupling with 4.3 gm (20 mmols) of Boc-Pro-OH analogous to Stage 3.

Stage 8

Coupling with 7.5 gm (30 mmols) of Boc-Leu-OH$\times H_2O$, post-coupling with 7.5 gm (30 mmols) of Boc-Leu-OH$\times H_2O$ analogous to Stage 3.

Stage 9

Coupling with 12.34 gm (30 mmols) of Fmoc-Asp($Bu^t$)-OH, first post-coupling with 12.34 gm (30 mmols) of Fmoc-Asp($Bu^t$)-OH, second post-coupling with 8.23 gm (20 mmols) of FMOC-Asp($Bu^t$)-OH analogous to Stage 3. The Fmoc group was split off with diethylamine/DMF (1:9) in 30 minutes' reaction.

Stage 10

Coupling with 5.9 gm (20 mmols) of Boc-Ser(Bzl)-OH, first post-coupling with 5.9 gm (20 mmols) of Boc-Ser(Bzl)-OH, second post-coupling with 5.9 gm (20 mmols) of Boc-Ser-(Bzl)-OH analogous to Stage 3.

II. Removal of peptide from the carrier with hydrazine 5 gm of peptide resin were stirred in a solution of 2.5 gm of hydrazinium hydroxide in 40 ml of DMF for 20 hours. The solution of the partially protected decapeptide hydrazide was then suction-filtered, and the resin was washed three times with a total of 20 ml of DMF. The DMF solution was added dropwise to anhydrous ether while stirring. The decapeptide derivative was thus flocculated. It was washed twice with ether, while being centrifuged, thereby partially eliminating the yellow byproducts. It was then dissolved again in 2 ml of DMF and 2 ml of methanol and again precipitated. Yield: 2.91 gm.

III. Purification of the partially protected decapeptide hydrazide by gel chromatography 2.9 gm of the partially protected decapeptide hydrazide were dissolved in 20 ml of methanol and chromatographed on Sephadex LH20 with methanol as the eluant (column: 5×86 cm). The fractions appearing after an elution volume of 350 ml were examined on silicagel plates in a chloroform/methanol/water/glacial acetic acid system (65:25:4:3) (spray reagent: chlorine/4,4'-bis(dimethylamino)diphenyl methane; hydrazide reagent: $K_3[Fe(CN)_6]/FeCl_3$). The majority of decapeptide hydrazide derivative appeared in the elution volume of from 590–723 ml (volume of fractions: 19 ml). After the fractions had been combined and the methanol had been evaporated, 2.24 gm of the partially protected decapeptide hydrazide were obtained, which still had a yellow coloration. This chromatography on Sephadex-LH20 eliminated the strongly hydrophilic impurities.

IV. Purification of the partially protected decapeptide hydrazide by reversed phase chromatography 2 gm of the partially protected decapeptide hydrazide were chromatographed on silicagel RP-8 (Merck ready-made column Lobar B, Lichroprep RP-8, Art. No. 11804) with methanol/water (90:10). The yellow by-products were eluted later than the peptide.

The identity of the partially protected decapeptide hydrazide obtained according to the preceding example was proven by aminoacid analysis, by the gas-chromatographic racemate test (see FIG. 1), and by $^{13}$C-NMR spectroscopic tests (see FIGS. 2*a* and 2*b*).

The aminoacid analysis was carried out in a Biotronik aminoacid analyzer LC 6000 E, and hydrolysis was effected with 6 N HCl at 110° C. over a period of 24 hours. Without correcting the hydrolysis losses, the following distribution of aminoacids was found:

TABLE 1

| Aminoacid | Number of aminoacid groups Found | Calculated |
|---|---|---|
| Asp | 1.00 | 1 |
| Thr | 0.84 | 1 |
| Ser | 1.12 | 2 |
| Glu | 1.00 | 1 |
| Pro | 0.94 | 1 |
| Gly | 1.00 | 1 |
| Leu | 1.78 | 2 |
| $NH_3$ | 0.85 | 1 |
| His | 1.00 | 1 |

The $^{13}$C-NMR spectra were measured in a WH-90 NMR-spectrometer made by Bruker-Physik of Karlsruhe, Germany, and the decapeptide hydrazide derivative was dissolved in methanol.

V. Removal of the decapeptide free from protective groups from the carrier 3 gm of dry, fully protected peptide resin were suspended in 10 ml of trifluoroacetic acid. After 10 minutes, 20 ml of 17% hydrogen bromide/glacial acetic acid solution were added. The reaction mixture, containing some thioanisole and resorcinol, was stirred for 2 hours in the dark at room temperature. After dilution with 20 ml of glacial acetic acid, the mixture was evaporated to half its volume in a rotary evaporator. After the addition of another 20 ml of glacial acetic acid, the resin was filtered off under exclusion of moisture. The clear yellow filtrate was again evaporated to about 10 ml and added dropwise, with stirring, to 100 ml of anhydrous ether. The slightly yellow precipitate of the peptide was washed twice with ether and then dissolved in 10 ml of water. The clear peptide solution (pH 1) was adjusted to pH 8.0 with aqueous sodium carbonate and then admixed with 2 ml of mercaptoethanol. The precipitate thus formed was again dissolved in 7 ml of DMF. After the addition of another 2 ml of mercaptoethanol, the mixture was stirred for 1 hour at pH 8.75. It was then extracted with 4 batches of 80 ml of ether. The aqueous phase was acidified to pH 4.8 with acetic acid and again extracted with 4 batches of 50 ml of ether.

VI. Chromatographic purification of the free decapeptide

The brownish-yellow peptide solution obtained above was chromatographed on Sephadex G-15 with 0.1 M acetic acid (column: 2.5×95 cm, elution rate 1 ml/min.). The peptide-containing fractions (10 ml) appearing after 185–300 ml and detected by thin-layer chromatography using the system 1-butanol/glacial acetic acid/water (3:1:1) were combined, lyophilized and chromatographed a second time. The peptide solution contained in the fractions 201–275 ml was concentrated by evaporation.

Yield: 2.24 gm.

300 mg of the yellow powder thus obtained were dissolved in 1.5 ml of methanol/water (9:1) and chromatographed on silicagel RP-8 (Lichroprep RP-8, Lobar column type C) (elution rate: 1 ml/min; volume of fraction: 6 ml). The peptide fraction contained in the elution volume from 376–424 ml was concentrated in vacuo and lyophilized.

Yield: 174 mg; $R_f$ 0.23 [silicagel, system: 1-butanol/glacial acetic acid/water (3:1:1)].

The identity of the decapeptide obtained in the preceding example was proven by $^{13}$C-NMR-spectroscopic tests (see FIGS. 3*a* and 3*b*) and by aminoacid analysis.

The aminoacid analysis was carried out in a Biotronik aminoacid analyzer LC 600 E. The hydrolysis was effected with 6 N hydrochloric acid at 110° C. over a period of 18 to 72 hours. Without correcting in hydrolysis losses, the following composition of aminoacids was found:

TABLE 2

| Aminoacid | Number of aminoacid groups Found | Calculated |
|---|---|---|
| Asp | 1.06 | 1 |
| Thr | 0.99 | 1 |
| Ser | 1.76 | 2 |
| Glu | 1.15 | 1 |
| Pro | 1.06 | 1 |
| Gly | 1.00 | 1 |
| Leu | 1.94 | 2 |
| His | 1.00 | 1 |

Investigation by gas chromatography, using the n-propyl ester of N-pentafluoropropionylamino acid of the total hydrolyzate of the decapeptide at the chiral phase Chirasil-Val [J. Chromatogr. 146, 197 (1978)] showed a very high enantiomeric purity of the aminoacid groups of the decapeptide (see FIG. 1).

The $^{13}$C-NMR spectra were measured in a WH-90 NMR spectrometer made by Bruker-Physik, Karlsruhe, Germany, at 30° C., solvent: $^2H_2O$ (See FIGS. 3*a* and 3*b*).

The novel decapeptide of the present invention and its hydroxide can be used as haptens which are coupled to a natural protein such as human serum albumin, cattle serum albumin, egg albumin or to a synthetic polypeptide such as poly-L-lysine, poly-L-alanyl-L-lysine or other carriers such as modified dextrans, using known methods. The peptide may also be coupled via other polyamines, such as 1,6-diaminohexane. An immunogen thus obtained, or the decapeptide itself, may be used according to known methods for the production of antisera or antibodies against human lymphoblast interferon.

The novel decapeptide may be used in a suitable preparation for therapy instead of human lymphoblast interferon.

The novel decapeptide is also useful as a tracer for the immunological determination of human lymphoblast interferon. For this purpose, it may, on the one hand, be labeled directly according to known methods, such as with radioactive iodine or other suitable markers, with enzymes such as peroxidases, or with fluorescent compounds. On the other hand, it may also be labeled by the same or similar methods in the form of the above-mentioned coupling products, and be used as a tracer.

The novel decapeptide can also be used in the form of a coupling product with an immobile carrier, such as dextran, sepharose or polystyrene, or modified inorganic carriers such as Biogel or CPG-10, for isolating and purifying antibodies against human lymphoblast interferons. Antibodies thus obtained can be used in known manner for the purification and isolation of human lymphoblast interferon.

The fully protected decapeptide deposited on the carrier after the stepwise synthesis can also be removed from the carrier by hydrolysis or exchange of ester radicals. The partially or fully protected decapeptide derivatives split off are also useful as intermediate products for the synthesis of higher peptides of lymphoblast interferon or for the synthesis of lymphoblast interferon itself.

The following examples describe various possible applications for the decapeptide of the present invention and the hydrazide thereof:

EXAMPLE A

Couplings with poly-L-lysine (a) With m-xylylene-diisocyanate 79 mg (62.5 nmols) of partially protected decapeptide hydrazide were dissolved in 3 ml of dioxane, and 1 ml of water at pH 7 was added thereto. 30 μl (about 200 nmols) of m-xylylene-diisocyanate were added thereto, while stirring. After 3 minutes, a solution of 50 mg of poly-L-lysine hydrobromide (mol. wt. 37,300) in 1 ml of water (pH 9.5, adjusted by means of 1 N sodium hydroxide solution) was added thereto. After 4 hours of standing at room temperature, about 20 ml of water were added, and the mixture was adjusted to about pH 7 with glacial acetic acid. The mixture was then evaporated in vacuo to half its volume and, after the addition of 20 ml of water, it was lyophilized.

Yield: 170 mg.

100 mg of the conjugate, dried over phosphorus pentoxide, were admixed with 2 ml of trifluoroacetic acid. After 10 minutes, 8 ml of 40% hydrogen bromide in glacial acetic acid (containing about 30 mg of resorcinol and 30 mg of thioanisole) were added to the suspension, and the mixture was stirred for 30 minutes in the dark at room temperature. After evaporation in vacuo the conjugate was precipitated by stirring the glacial acetic acid solution into absolute ether (about 100 ml). After washing twice with 100 ml-batches of ether in a centrifuge glass, the precipitate (180 mg) was dissolved in water and dialyzed against 1 N acetic acid for 24 hours and then against distilled water for 24 hours (exclusion limit 8000). After centrifugation of the dialyzate, 31 mg of water-insoluble conjugate were obtained, containing 6.4 mol of decapeptide hydrazide per mol of poly-L-lysine. 1.7 mg of soluble conjugate with a charge of 42:1 can be obtained from the aqueuos solution after lyophilization.

(b) By azide coupling 70 mg (50 μmols) of partially protected decapeptide hydrazide were dissolved in 1.5 ml of DMF, and at −20° C. 70 μl (126 μmols=2.5 equivalents) of 1.8 NHCl/ethyl acetate were added. At −20° C., first 8 μl (60 μmols=1.2 equivalents) of isoamyl nitrite, and after 5 minutes, at −10° C., another 2 μl of isoamyl nitrite were added until blue coloration was obtained with potassium iodide/starch paper. After 10 minutes at −10° C., an ice-cold solution of 70 mg of poly-L-lysine hydrobromide in 0.5 ml of water (adjusted to pH 9 with 4 μl of triethylamine) was added. The solution became turbid. After 20 minutes, the solution was adjusted to pH 8.5 with another 6 μl of triethylamine, and the resulting very turbid, viscous solution was stirred at −10° C. for 30 minutes and then kept at +4° C. for 18 hours. Thereafter, it was stirred for another 8 hours at room temperature, then adjusted to pH 6 with 10% acetic acid and, after the addition of a large quantity of tert. butanol and some water, it was lyophilized. To split off the protective groups, the procedure described in (a) was used. 36.5 mg of colorless conjugate, readily soluble in water, were obtained, containing 14.9 mols of decapeptide per mol of poly-L-lysine.

EXAMPLE B

Iodine labeling of the coupling product of the decapeptide or the hydrazide thereof with poly-L-lysine 2 mg of the dried coupling product were weighed out and dissolved in 25 μl of water. This solution was diluted with 0.1 mM of sodium borate buffer, pH 9, until the concentration of the coupling product was 10 μgm/μl. 12 μl thereof with a borate concentration of 0.1 M, pH 9.0, and of the coupling product with 10 μgm/μl were transferred at a temperature of 0° C. (on ice) into a reaction vessel in which BOLTON-HUNTER reagent (N-hydroxy-succinimide ester of p-hydroxyphenylpropionic acid iodized with $^{125}I$) had been dried with benzene.

After 1 hour, the reaction was stopped by adding 90 μl of 0.3 M glycine in 0.1 M sodium borate, pH 9.0. After another 10 minutes, the entire volume was poured onto a chromatography column [7 ml bed volume, Sephadex G 25 Medium (Pharmacia, Uppsala)], which had been equilibrated with 50 mM sodium phosphate, pH 7.5, and 0.25% gelatin and which was also developed in this buffer. The high-molecular labeled substance was separated from any low-molecular radioactive reaction products and appeared in the first fractions of the void volume.

A better yield, compared with these original instructions laid down by Bolton and Hunter, was obtained when the solution was adjusted to an acidic pH after the reaction had come to an end. After the addition of glycine, the pH was adjusted from 9 to 4 by further addition of 100 μl of 20 mM sodium acetate, pH 4.0. The chromatography column was pretreated accordingly with 20 mM sodium acetate, pH 4.0, and 0.25% gelatin and was developed in this buffer.

Starting from a radioactivity of 0.2 mCi of a BOLTON-HUNTER reagent with a specific radioactivity of 2000 Ci/mmol, a labeling of at least $3\times10^5$cpm (counts per minute)/μg of coupling product was obtained.

EXAMPLE C

Coupling to AH-Sepharose 4B for the preparation of materials for affinity chromatography 35 mg (25 μmols) of partially protected decapeptide hydrazide were dissolved in 2 ml of trifluoroacetic acid and admixed with 4 ml of 33% hydrobromic acid/glacial acetic acid. After one hour, the mixture was evaporated in a rotary evaporator, the residue was taken up in 2 ml of glacial acetic acid, and the solution was added dropwise, while stirring, to 50 ml of anhydrous ether. The precipitate was removed by centrifuging and dried in vacuo over solid potassium hydroxide. The unprotected decapeptide hydrazide dihydrobromide thus obtained was converted into the azide analogous to Example A(b), and in DMF/water it was coupled to the amino groups of 300 mg of AH-sepharose 4B. After 24 hours' reaction, the AH-sepharose 4B decapeptide was washed with DMF, dioxane and water until no low-molecular constituents were detectable by thin-layer chromatography.

EXAMPLE D

Coupling of the decapeptide to lysine-sepharose 4B for affinity chromatography 35 mg of partially protected decapeptide hydrazide were treated with hydrogen bromide/trifluoroacetic acid, as described in Example C, and converted into the azide which was coupled to 300 mg of lysine-sepharose 4B (Pharmacia).

EXAMPLE E

Preparation of coupling products of decapeptide to aminopropyl-CPG-10 for affinity chromatography 500 mg of Controlled Pore Glass CPG 10 (pore size 75 and 120 Å, charged with aminopropyl groups) were coupled with the azide obtained from 70 mg of partially protected decapeptide hydrazide, analogous to Example C.

EXAMPLE F

Linking of two molecules of decapeptide hydrazide by means of 1,6-diamino-hexane 70 mg (50 μmols) of partially protected decapeptide hydrazide were converted into the azide as described in Example A(b). At −10° C., 2.9 mg (25 μmols) of 1,6-diaminohexane in 200 μl of DMF were added to the azide. After adjusting the mixture to about pH 8.5 with triethylamine, it was stirred for 2 hours at −10° C., allowed to stand for 24 hours at 4° C. and stirred for 8 more hours at room temperature. The reaction solution was then added dropwise to anhydrous ether, while stirring. The precipitate formed thereby was washed twice with ether and dried over diphosphorus pentoxide/potassium hydroxide. It was then dissolved in trifluoroacetic acid and admixed with 4 ml of 33% hydrogen bromide/glacial acetic acid. The product free from protective groups was precipitated with ether after 2 hours, dried over potassium hydroxide and then chromatographed in DMF on Sephadex LH 20 (column 1×90 cm). The first eluted fractions containing the dimer (detected by thin-layer chromatography) were evaporated to dryness in vacuo.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. The decapeptide of the formula H-Ser-Asp-Leu-Pro-Gln-Thr-His-Ser-Leu-Gly-OH.

2. The decapeptide hydrazide of the formula Boc-Ser(Bzl)-Asp($Bu^t$)-Leu-Pro-Gln-Thr(Bzl)-His-Ser(Bzl)-Leu-Gly-$NHNH_2$.

3. The decapeptide hydrazide of the formula H-Ser-Asp-Leu-Pro-Gln-Thr-His-Ser-Leu-Gly-$NHNH_2$.

4. The method of using the decapeptide of claim 1 as a hapten, tracer or antibody.

5. The method of using the decapeptide hydrazide of claim 2 for the preparation of higher peptides of lymphoblast interferon or for the preparation of lymphoblast interferon.

6. The method of using the decapeptide hydrazide of claim 3 as a hapten, tracer or antibody.

* * * * *